United States Patent [19]

Sigler et al.

[11] Patent Number: 4,654,007
[45] Date of Patent: Mar. 31, 1987

[54] PORCELAIN DENTAL RESTORATION METHOD

[75] Inventors: Roger M. Sigler, Parkville; Timothy J. Sigler, St. Joseph, both of Mo.

[73] Assignee: Myron International, Inc., Kansas City, Kans.

[21] Appl. No.: 734,326

[22] Filed: May 15, 1985

[51] Int. Cl.$^4$ ............................................. A61C 5/00
[52] U.S. Cl. .................................. 433/236; 433/215
[58] Field of Search ................ 433/215, 212, 199, 226

[56] References Cited

U.S. PATENT DOCUMENTS

| | | | |
|---|---|---|---|
| 856,034 | 6/1907 | Crouse | 433/228 |
| 866,305 | 9/1907 | Roach . | |
| 1,712,043 | 5/1929 | Limbarth . | |
| 1,772,027 | 8/1930 | Baumgarten . | |
| 2,196,258 | 4/1940 | Erdle . | |
| 3,004,343 | 10/1961 | Rydin . | |
| 3,046,657 | 7/1962 | Menter et al. . | |
| 3,375,582 | 4/1968 | Myerson . | |
| 3,422,535 | 1/1969 | Johnson . | |
| 3,423,829 | 1/1969 | Halpern et al. . | |
| 3,423,831 | 1/1969 | Semmelman . | |
| 3,449,832 | 6/1969 | Connan . | |
| 3,464,837 | 9/1969 | McLean et al. . | |
| 3,468,028 | 9/1969 | Sunter . | |
| 3,471,927 | 10/1969 | Eisenberg . | |
| 3,481,772 | 12/1969 | MacNairn et al. . | |
| 3,483,618 | 12/1969 | Andrew . | |
| 3,488,846 | 1/1970 | Cornell . | |
| 3,647,488 | 3/1972 | Brigham et al. . | |
| 3,647,498 | 3/1972 | Dougherty . | |
| 3,649,732 | 3/1972 | Brigham et al. . | |
| 3,760,502 | 9/1973 | Hirsch . | |
| 3,826,778 | 7/1974 | Dietz . | |
| 4,089,830 | 5/1978 | Tezuka et al. . | |
| 4,104,798 | 8/1978 | Takahashi et al. . | |
| 4,129,946 | 12/1978 | Kennedy . | |
| 4,194,907 | 3/1980 | Tsai . | |
| 4,210,447 | 7/1980 | Tsai . | |
| 4,378,248 | 3/1983 | Griffith | 106/35 |
| 4,473,353 | 9/1984 | Greggs | 433/215 |
| 4,475,892 | 10/1984 | Faunce . | |

FOREIGN PATENT DOCUMENTS 2078707A 7/1981 United Kingdom .

OTHER PUBLICATIONS

Raptis-Fan-Powers-Properties of Microfilled and Visible Light-Cured Composite Resins, 1/79; Dental Survey; Esthetic Tooth Restoration; Barkle-Gaw-Faunce.
Bowen; JAD, vol. 74, Feb. 1967, pp. 439–445-Adhesive Bonding of Various Materials to Hard Tooth Tissues.
Goteiner-Sonnenberg; Clinical Preventive Dentistry; vol. 4, No. 1, Jan.-Feb. 1982; pp. 9–12; Maintenance of Laminate Veneers.
Slocum; The Dental Digest pp. 96–98; Indirect Gold Inlay Technic.

(List continued on next page.)

Primary Examiner—Robert Peshock
Attorney, Agent, or Firm—Schmidt, Johnson, Hovey & Williams

[57] ABSTRACT

An improved method of porcelain dental restoration is provided which gives strong, aesthetically pleasing restorations in a wide variety of contexts such as inlays, onlays or overlays. The method involves first preparing a tooth requiring restoration by removing the decayed portions and exposing dentin surface, whereupon a lining material (e.g. a glass ionomer) is applied to the exposed dentin. An impression of the patient's teeth is next taken, whereupon a refractory positive impression of the prepared tooth is fabricated. Next, a porcelain restoration is produced by appropriate layering and firing to give a restoration piece which substantially conforms to the shape of the originally decayed portion of the tooth. Finally, the porcelain restoration is fused to the natural tooth by means of fusing cement system which mechanically and chemcially bonds to porcelain, lining cement and adjacent enamel surfaces. The resultant dental restoration produces a restored tooth having a strength approaching that of the original tooth.

9 Claims, 16 Drawing Figures

OTHER PUBLICATIONS

Johnson; Pediatric Dentistry vol. 4, No. 1, pp. 32-37; Use of Laminate Veneers in Pediatric Densitry; Present Status and Future Developments.

Boyer-Chalkley; J. Dent. Res 61(3); 489-492-Mar. 1982; Bonding Between Acrylic Laminates and Composite Resin.

Heyde-Cammarato; Dental Clinics of North America--vol. 25, No. 2, Apr. 1981, pp. 337-345; A Restorative System for the Repair of Defects in Anterior Teeth.

Wickwire-Rentz; Am. J. Orthod. Nov. 1973, vol. 64, No. 5; Enamel Pretreatment: A Critical Variable in Direct Bonding Systems.

Gianelly-Valentini; Rationale of Three-Premolar Extraction: A Case Report.

Rasmussen; j. Dent Res. 57(1):11-20, Jan. 1978; Fracture Studies Adhesion.

Gjfrdent-Espevik; J. Dent 57(1) 21-26 Jan. 1978; Corrosion and Creep of Dental Amalgam.

1/79; Dental Survey; Esthetic Tooth Restoration; Barkley-Gaw-Fauce.

PORCELAIN DENTAL RESTORATION METHOD

BACKGROUND OF THE INVENTION

1. Field of the Invention

The present invention is broadly concerned with a greatly improved dental restoration method making use of asthetically pleasing fired porcelain restoration pieces such as inlays, onlays or crown overlays. More particularly, this concern with such a method wherein only a minimum amount of the original tooth structure is disturbed or removed, while nevertheless creating a restoration which is permanent and has a strength approaching that of the natural tooth.

2. Description of the Prior Art

Restorative dentistry has been practiced for decades, and as a consequence a wide of variety of procedures and materials have been employed. To give but one example, for many years gold was the material of choice for full crown restorations, whereas other alloys have typically been used in the context of inlays and onlays. While such materials generally exhibit good wear characteristics, they are deficient in a number of respects. Thus, these materials do not give the most pleasing visual effect in the mouth of the patient, and therefore are deemed deficient. Moreover, the coefficient of expansion of such metallic materials is obviously greatly different than that of the natural tooth structure, and this can lead to significant problems.

In addition to metallic restorations, attempts have been made in the past to make use of synthetic resin materials, various ceramics and porcelains. Here again though, these techniques have not met with a great deal of success. One problem typically encountered is the fact that the strength of the restored tooth is significantly less than that of the original tooth structure, and as a consequence the restoration can rather easily be broken or detached from the underlying tooth structure. Further, in some instances where attempts were made to use ceramics or porcelains, the attaching adhesive employed was subject to erosion in the moist conditions of the mouth, and this led in early failures of the restorations.

Another common problem with prior dental restoration techniques stems from the fact that, for purposes of attachment, it has been necessary to remove a substantial fraction of the original tooth structure. This is particularly the case for crown overlays, where typically only a relatively small stub of the original tooth structure is maintained. These procedures violate a cardinal principle of restorative dentistry, i.e., that only this minimum amount of original tooth structure should be disturbed in order to accomodate the desired restoration.

In light of the foregoing, it will be appreciated that there is a decided need in the art for a dental restoration method which combines the goals of minimum tooth structure removal with a strong, permanent restoration and a pleasing final appearance for the patient.

SUMMARY OF THE INVENTION

The present invention overcomes the problems noted above and provides a greatly improved dental restoration method which makes use of porcelain restoration pieces which can be configured and given an appearance closely matching that of the patients original teeth. Moreover, the method of the invention provides an essentially permanent, strong restoration which is not subject to rapid erosion in the mouth of the patient. In many cases complete restorations in accordance with the invention have a strength of from 65 to 85 percent of that of the original natural tooth structure.

Broadly speaking, the method of the present invention for restoring a decayed tooth involves the steps of first removing the decayed portion of the tooth and leaving dentin surface exposed. A lining material is then applied to the exposed dentin surface with the cement being characterized by the properties of bonding to the dentin surface and of serving as a fusible substrate for attachment of a porcelain restoration thereto. The initial preparative steps are typically performed by the dentist in his office. Thereafter, the dentist makes a negative impression of the patients teeth (either uppers or lowers as the occasion requires, or more desirably both an upper and a lower so that proper articulation and fit can be readily assured). The dentist may also make a positive impression of the patients teeth using conventional materials or techniques, or the negative impressions can be sent to a dental lab.

In any event, at the dental lab the positive impression is used as a model to produce a refractory positive impression of the previously prepared tooth needing restoration. Using this refractory positive, the lab fabricates a porcelain restoration substantially conforming to the removed portion of the tooth requiring restoration. This step typically involves a layering of porcelain material with successive firings as necessary. After the porcelain restoration is checked for accuracy in the lab, it is acid etched and returned to the dentist for installation in the patients mouth. This procedure commonly involves an initial acid etching of the prepared tooth, so as to create microscopic surface irregularities which facilitate ultimate fusion of the restoration to the tooth. Thereupon, an appropriate adhesive system or cement is applied between the underside of the restoration and the lining cement and enamel of the previously prepared tooth, and the restoration is pressed into place and allowed to cure, usually using light.

In this connection, a prime feature of the present invention resides in the fact that the final adhesive creates an actual fusion of the porcelain restoration to the underlying tooth structure. This fusion occurs by virtue of mechanical and chemical bonding between the porcelain restoration and the lining material and the enamel forming a part of the underlying tooth. This fusion is to be contrasted, for example, with prior low strength dental adhesives which provide primarily a mechanical bond between the tooth structure and a restoration piece.

In particularly preferred forms, the lining material comprises a glass ionomer and particularly good results have been achieved with a products of this type sold by GC International Company of Phoenix, Ariz.

Alternately, use can be made of a glass ionomer—amalgum mixture (e.g., 15 grams glass ionomer, 17 grams analygum alloy—combined as powder and added to 10 grams of liquid polyocrylic acid) The initial decay removal step of the method hereof can be performed by any appropriate technique, such as by conventional drilling. On the other hand, the present invention also comprehends the use of a caries removal material. Indeed, the present invention permits use of such materials even though the resultant tooth may be rendered relatively irregular by such use. That is to say, the porcelain restorations in accordance with the inven-

DESCRIPTION OF THE PREFERRED EMBODIMENTS

The most preferred methods in accordance with the present invention are set forth in the following illustrative example. It is to be understood, however, that the example is presented for purposes of illustration only, and nothing therein is to be taken as a limitation upon the overall scope of the invention. Thus, while restoration of the occlusal surface of a molar is specifically described, it will be appreciated that the invention is not limited to this type of procedure, but rather pertains to virtually any restoration involving an inlay, an onlay, or full crown overlay. Moreover, preferred techniques described can be modified as the need arises in many respects without departing from the principles of the invention.

EXAMPLE

The following example sets forth the most preferred procedures in accordance with the present invention. This example is given with reference to the accompanying drawings in order to facilitate a complete understanding of the invention.

In the illustrated embodiment a restoration of the occlusal surface of a decayed molar is depicted; it is to be understood, however, that the invention is not limited to this type of restoration, but rather finds application in all types of onlay, inlay, and crown overlay restorations.

Figure 1:
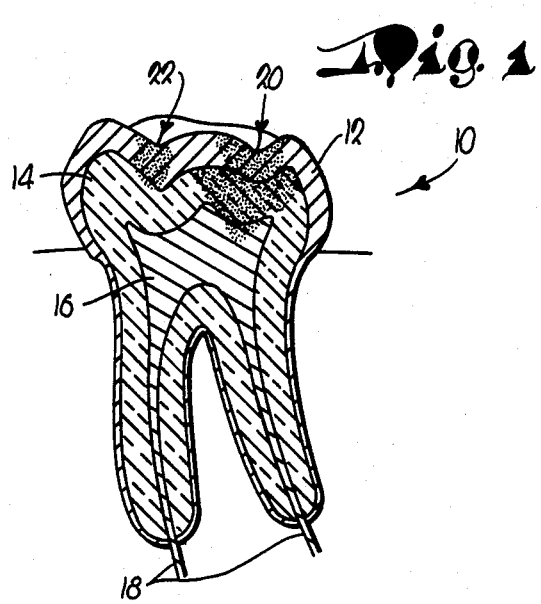
FIG. 1 is an enlarged, sectional view of a decayed tooth in need of restoration.
Figure 2:
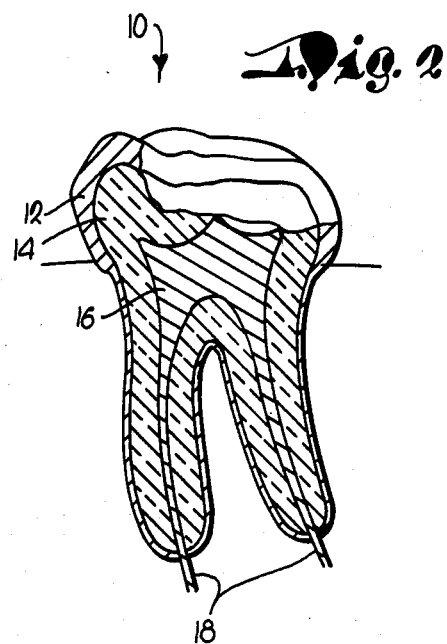
FIG. 2 is a sectional view similar to that of FIG. 1, but showing the figuration of the tooth after the decayed portion has been removed and pulp and dentin surfaces are exposed.

Referring first to FIG. 1, a molar 10 is illustrated. The molar includes outermost enamel 12, inner dentin region 14, and innermost pulp 16 with roots 18. The tooth is decayed as at 20, 22, such decay in one area extending through the enamel 12 and dentin 14, and into pulp 16.

The dentist first removes the decay from tooth 10 by conventional techniques, assuring that only the minimum of tooth is removed. In this regard the dentist may use standard drilling techniques, or employ a caries removal material such as the Caridex TM product sold by Princeton Dental Products, Inc. of New Brunswick, N.J. Caries removal products can be used to good advantage in the invention inasmuch as the restoration provided can readily accommodate the often irregular surfaces left after removal of decay. Thus the restoration method of the invention and caries removal materials can be used in conjunction to minimize patient discomfort and the need for anesthesia.

Figure 3:
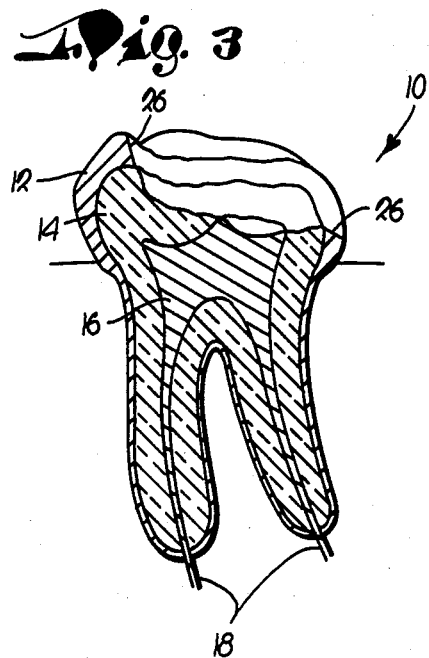
FIG. 3 is a view similar to that of FIG. 2, but illustrating beveling of the outermost enamel surfaces of the tooth to facilitate attachment of a restoration.
Figure 4:
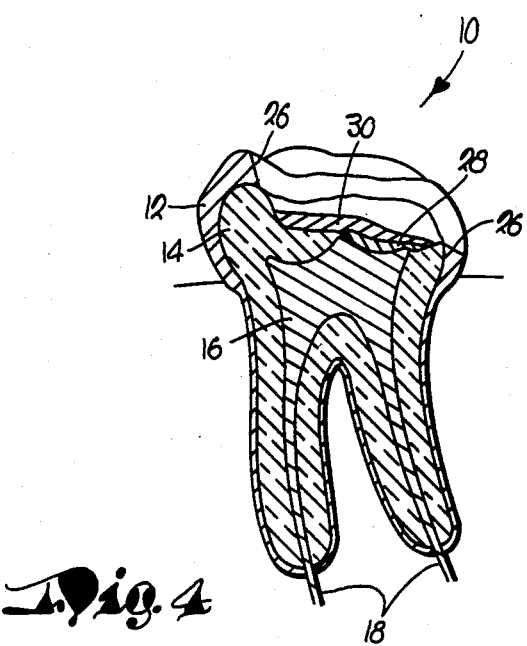
FIG. 4 is a view similar to that of FIG. 3, illustrates application of a pulp desensitizing material and a lining material to the tooth structure.

The next step in the operation involves beveling of the enamel surface 12, as at 26, in order to establish an enlarged, smooth, blended surface for ultimate attachment of a molded porcelain restoration. This step is depicted in FIG. 3.

The clinician next applies a pulp desensitizing material 28 to the exposed surfaces of the pulp 16, in order to insure that the sensitive pulp is protected to minimize patient discomfort. Following this, a layer of lining material such as glass ionomer lining cement 30 or an ionomer—amalgum mixture is applied over the material 28 and is secured to the dentin 14 (see FIG. 3). The preferred glass ionomer lining cement is sold by G. C. International Company of Phoenix, Ariz. The ionomer cement is supplied as a two component product, namely a powdered component and a liquid component. The powder comprises aluminofluorosilicate glass containing $SiO_2, Al_2O_3, CaF_2$ and $Na_3PO_4$. The liquid component on the other hand comprises 60% water and 40% polyacrylic acid. The manufacturer advises that the two components be mixed at a ratio of 1.2 grams of the powdered component to 1 gram of the liquid component, and that the mixed cement be applied only on a "dry field." However, experience in the field indicates that clinicians may vary the ratio of the two components as the need arises.

In any event, the purpose of the lining material is to provide a material that will adequately bond to the dentin layer, and which will thereafter permit fusible attachment of the porcelain restoration.

Figure 5:
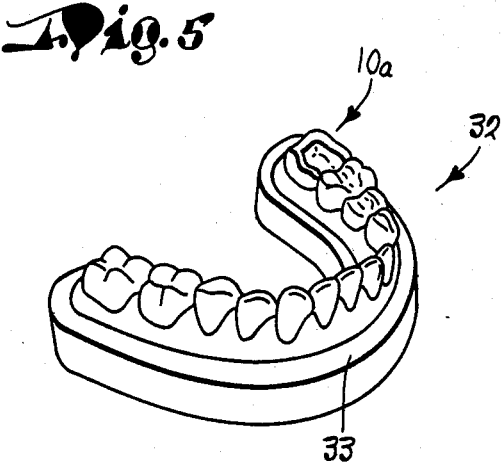
FIG. 5 illustrates a positive impression made of the patients mouth, with the previously prepared tooth depicted in FIG. 4 being included in the impression.

As illustrated in FIG. 5, a positive impression 32 of the patients teeth is next made (either an upper or lower, or both). This involves only conventional procedures well known to those skilled in the art. Typically, the dentist may make only a negative impression of the patients teeth, and the dental lab may make a positive therefrom. Alternately, the dentist could supply a positive to the dental lab.

Figure 6:
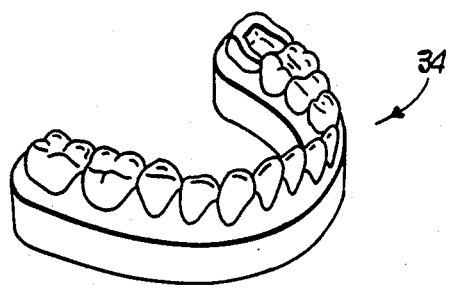
FIG. 6 is a view similar to that of FIG. 5, but illustrates the positive impression after removal of the surrounding flange, in order to permit insertion of the positive impression into a dental tray.

In any event, the impression 32 includes an impression 10a of the previously treated tooth 10. The positive 32 is typically formed of plaster of paris, and includes a ridge or flange 33 (FIG. 5). In the next step (FIG. 6), the ridge or flange 33 is ground away, leaving a final positive impression 34 which is used in succeeding steps.

Figure 7:
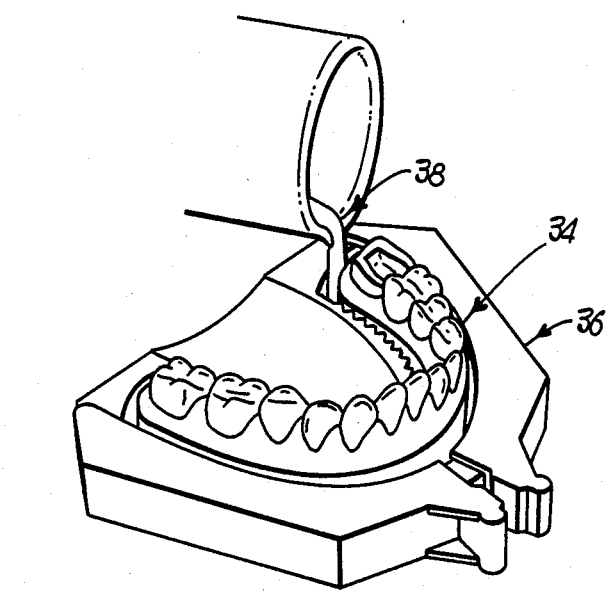
FIG. 7 illustrates the positive impression situated within a dental tray, with stone material being poured into the tray.
Figure 8:
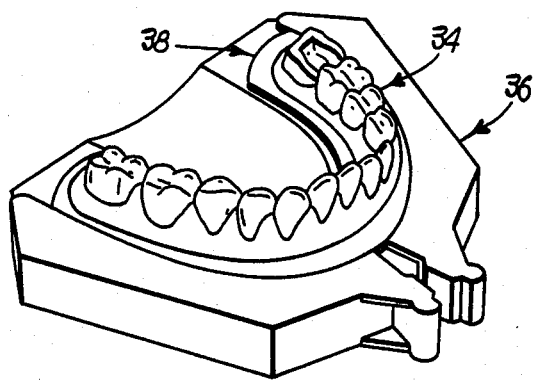
FIG. 8 is a view similar to that of FIG. 6, illustrates the positive impression within the tray, the latter being filled with stone material.

FIG. 7 illustrates the positive impression 34 situated within a conventional dental lab tray 36. Moreover, the step of applying refractory material 38 into the tray and surrounding relationship to the impression 34 is also depicted. A variety of specific refractory materials can be used in this context, but it is preferred to employ Mirage investment material commercialized by the Myran's Dental Laboratories of Kansas City, Kansas such material being specifically formulated for the Mirage restorative technique of this invention. This investment material is a phosphate-based substance which is supplied in two components, namely a liquid and a powder. The material should be mixed and employed in accordance with manufacturers recommendations. FIG. 8 illustrates the tray 36 and impression 34 after the investment material 38 has been fully poured into the tray.

Figure 9:
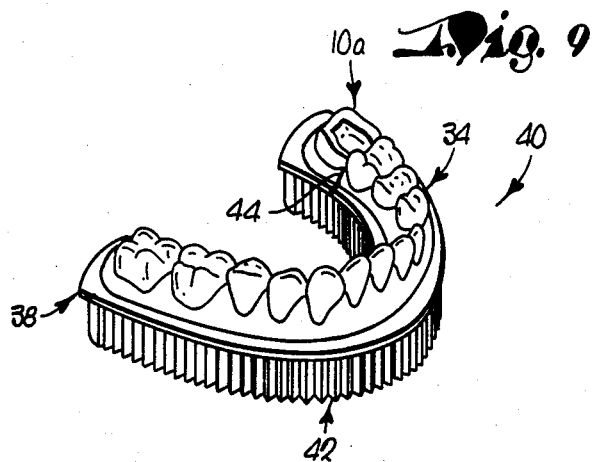
FIG. 9 illustrates the stone composite obtained from the tray depicted in FIGS. 7 and 8, and with the positive impression of the tooth requiring restoration being ditched from the composite.

FIG. 9 illustrates the completed casting 40 derived from the tray 36 of FIG. 8. It will be seen in this respect that the overall casting 40 includes the impression 34 as well as a ribbed, depending investment portion 42. In addition, as seen in FIG. 9, the positive impression 10a of the tooth 10 is "ditched", i.e., the impression 10a is cut from the remainder of the overall impression along cut line 44.

Figure 10:
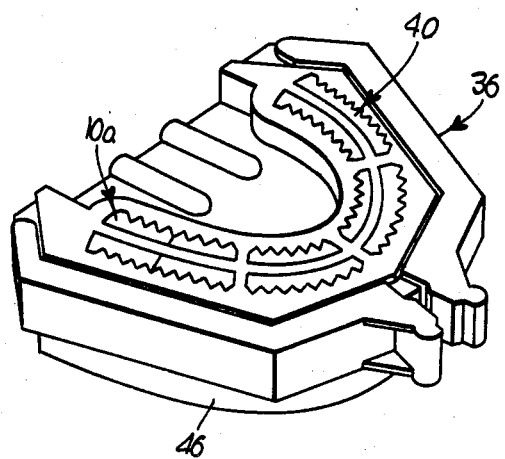
FIG. 10 illustrates the next step in the overall procedure involving placement of the ditched composite into a dental tray, the latter being inverted and placed in a lower tray filled with plastizied impression material to produce a negative impression.
Figure 11:
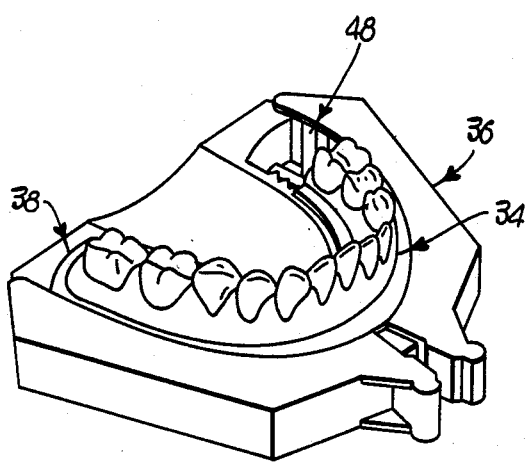
FIG. 11 illustrates the tray and composite, with the ditched positive impression of the tooth requiring restoration being removed.
Figure 12:
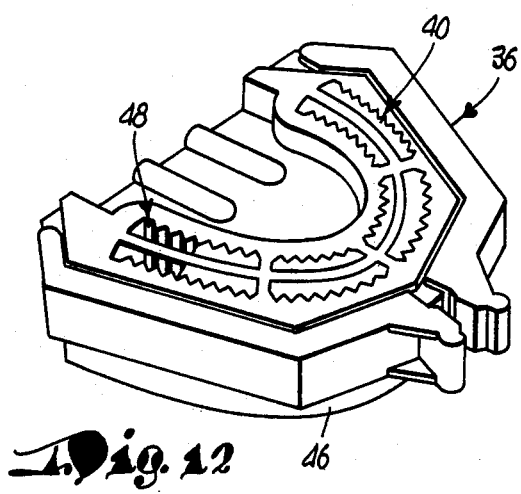
FIG. 12 illustrates the next step in the procedure wherein the trayed composite with the ditched impression removed placed over the lower tray including the previously made negative impression.
Figure 13:
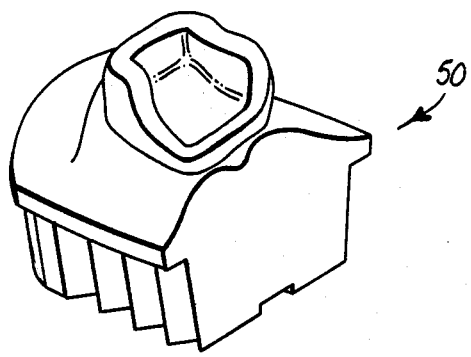
FIG. 13 is a perspective enlarged view of a refractory positive fabricated using the set-up illustrated in FIG. 12.
Figure 14:
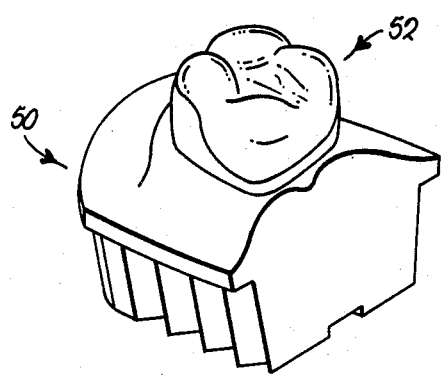
FIG. 14 is a perspective view similar to that of FIG. 13, but illustrates built-up porcelain restoration piece on the refractory positive depicted in FIG. 13.

In the next step, (see FIG. 10), the segmented body 40 is placed again within the tray 36, and the filled tray is inverted so as to place the ditched positive impression 34 within a lower tray 46. The lower tray 46 is filled with plastisized impression material of conventional makeup, in order to produce a negative impression in the tray 46. The filled tray 36 is next removed (see FIG. 11), and at this time the positive impression 10a with the depending investment materials secured thereto, is removed from the tray, thereby leaving an opening 48. The tray 36 is then replaced above the lower tray 46 including the negative impression, so that the opening 48 is situated above the negative impression of the decayed tooth requiring restoration. At this point "Mirage" refractory material of the type described is poured into the opening 48, in order to create a refractory positive which matches the positive impression 10a. After appropriate firing and curing, a final refractory positive 50 corresponding to the positive impression 10a is obtained. The impression 50 may then be articulated with the remainder of the impression 34, to insure that a faithful impression has been produced.

Figure 15:
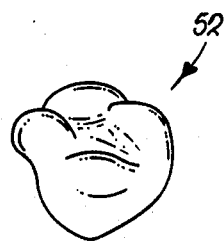
FIG. 15 is a perspective view of the porcelain restoration piece after final firing and polishing thereof.

In the next step, a porcelain restoration piece 52 is produced on the investment positive 50 which sustantially conforms to the shape of the removed decayed portion of the original tooth 10, in order to permit full restoration of the tooth to essentially its original configuration. A wide variety of porcelain materials can be used in fabricating the restoration piece 52, typically a simple low fusing ceramic material fired at 1800° F. may be employed. Also, conventional materials may be added to create fluorescence in the finished restoration in order to enable the finished piece 52 to match natural dentition under various lighting conditions. The porcelain technique involved in building up the porcelain restoration 52 are conventional and within the skill of the art. Basically however, the positive 50 is first submerged in condensor liquid whereupon excess moisture is removed by blotting. The porcelain is next mixed with the condensor to provide a thick consistancy which will slide very slowly off a metal spatula, whereupon the porcelain is applied. Care must be used not to strike the model with metal instruments during porcelain application, in that this may leave behind iron oxides resulting in black lines in the final porcelain restoration. A vibrating brush may be employed to build up the porcelain piece on the impression 50, and here again use of this type of brush is known in the art. Firing the built up porcelain should result in an outer surface which is glazed in appearance. In many instances, successive layering and firing of porcelain material is employed to achieve a final desired restoration piece. When the restoration piece 52 is produced having the desired final configuration, a thin layer of porcelain is applied with a final firing in order to give the restoration a desired natural appearance. The porcelain restoration 52 is then divested from the impression 50 by means of glass bead blasting, (see FIG. 15). The finished restoration 52 is then checked using the original positive 32, and any minute imperfections in the restoration 52 can be remedied by appropriate grinding and repolishing to reestablish the surface glaze. At this point the internal surface (underside) of the restoration is acid etched for 2 minutes with an acidic solution containing 1,111 ml. distilled $H_2O$, 2,000 ml. 37% HCL, 667 ml. of 70% $HNO_3$ and 222 ml. of 48% HF.

Figure 16:
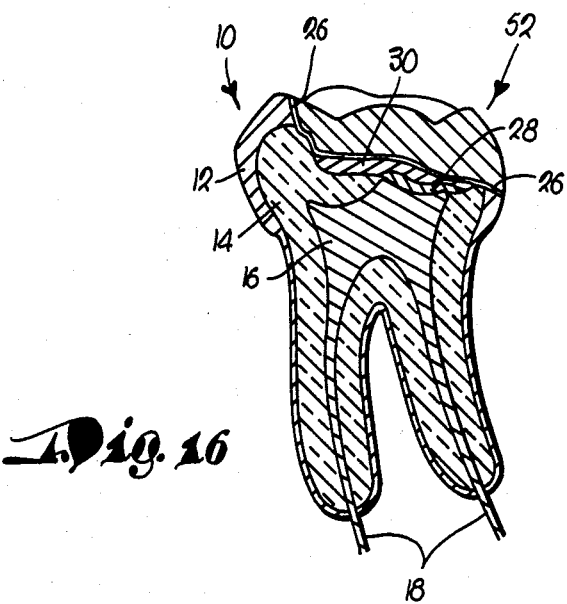
FIG. 16 is a sectional view similar to that of FIG. 1, but showing the porcelain restoration in place on the previously prepared tooth.

The acid etched porcelain restoration 52 is then returned to the dentist who applies it to the previously prepared tooth 10. In this regard (see FIG. 16), the restoration 52, if properly made, will be completely complementary with the prepared surface of the tooth 10. In the first step of the attachment process, the glass ionomer lining material and exposed beveled enamel of the tooth 10 are lightly etched using a mild solution (e.g., about 10%) of phosphoric acid, in order to create microscopic surface irregularities which facilitate ultimate mechanical retention and chemical fusion of the porcelain restoration to the tooth. Next, an appropriate fusing cement (for example, an unfilled BIS-GMA composite resin or dentin bonding agent) is applied to the glass ionomer 30 dentin 14 and beveled surfaces 26 of the enamel 12. The acid etched restoration 52 is then coated with a silane coupler and allowed to set. A thin layer of BIS-GMA microfilled composite resin is placed on the tooth and the underside of the porcelain restoration. The restoration is then placed on the prepared surface of the tooth and is pressed into place and is light cured in place for 20-40 seconds. This serves to actually fuse the porcelain restoration to the structure of the tooth through a mechanical and chemical bonding between the porcelain, fusing cement, ionomer lining cement, and tooth enamel. The result is an extremely strong, permanent restoration which is very close in appearance to the original tooth.

Those skilled in the art will appreciate that a number of variations and changes can be made in the preferred methods hereof without departing from the spirit and scope of the invention. Such changes may include differences in specific method steps and/or materials, so long as the essentials of the invention are satisfied. It is, of course, intended to cover all such variations and changes within the ambit of the invention.

We claim:

1. A dental restoration method for restoring a decayed tooth, comprising the steps of:
    removing the decayed portion of said tooth, and leaving dentin surface and enamel margin exposed;
    applying lining material in protective, covering relationship to said dentin while leaving at least a portion of said enamel margin exposed, said lining material lining characterized by the properties of bonding to said dentin surface and of serving as a fusible substrate for attachment of an acid-etched porcelain restoration thereto;
    fabricating a porcelain restoration substantially conforming to the removed portion of said tooth, and acid etching the underside of said restoration; and
    applying a fusing cement between the underside of said restoration and both said lining material and enamel margin, and fusing the restoration to the lining material and the enamel margin.

2. The restoration method of claim 1, said lining material comprising a glass ionomer lining cement.

3. The restoration method of claim 1, said decay removal step comprising the step of drilling decay from the tooth.

4. The restoration method of claim 1, said decay removal step comprising step of applying a caries removal material to the decayed portion of said tooth.

5. The restoration method of claim 1, said fabricating step comprising the steps of:
    making a positive impression of said tooth with the decayed portion thereof removed;
    applying porcelain material to said positive impression, firing said porcelain material to create a final porcelain restoration; and
    separating the fired porcelain restoration from said positive.

6. The restoration method of claim 1, including the step of acid etching said enamel margin and lining material prior to said application of fusing cement.

7. The restoration method of claim 1, said porcelain restoration being selected from the group consisting of onlays, inlays and crown overlays.

8. The method of claim 1, said fusing cement comprising a silane coupler applied to the underside of said restoration, and a layer of BIS-GMA filled composite resin applied between said underside and said enamel and lining material.

9. In a dental restoration method for restoring a tooth having a portion thereof missing as compared with the tooth in a virgin state, said tooth being in a condition with said portion missing and with dentin surface and enamel margin exposed, said method comprising the steps of:
    applying lining material in protective, covering relationship to said dentin while leaving at least a portion of said enamel margin exposed, said lining material lining characterized by the properties of bonding to said dentin surface and of serving as a fusible substrate for attachment of an acid-etched porcelain restoration thereto;
    fabricating a porcelain restoration substantially conforming to the missing portion of said tooth, and acid etching the underside of said restoration; and
    applying a fusing cement between the underside of said restoration and both said lining material and enamel margin, and fusing the restoration to the lining material and the enamel margin.

* * * * *